United States Patent [19]

Cehovic et al.

[11] Patent Number: 5,019,558

[45] Date of Patent: May 28, 1991

[54] METHOD FOR TREATING MEMORY DISTURBANCES USING ARGININE ASPARTATE

[76] Inventors: Georges Cehovic, 7 rue de La Vallé, 91120 Palaiseau; Emmanuel Panconi, Rue de Maréchal Gallieni, 33700 Merignac, both of France

[21] Appl. No.: 191,391

[22] Filed: May 9, 1988

[51] Int. Cl.$^5$ .................. A61K 37/00; A61K 31/33
[52] U.S. Cl. ........................... 514/11; 514/183
[58] Field of Search ............... 514/11, 183

[56] References Cited

FOREIGN PATENT DOCUMENTS 0873265  9/1961  France .
1625M   12/1962  France .
2568124  7/1984  France .

*Primary Examiner*—Stanley J. Friedman
*Assistant Examiner*—Gary E. Hollinden
*Attorney, Agent, or Firm*—Oblon, Spivak, McClelland, Maier & Neustadt

[57] ABSTRACT

A method for treating memory disturbances comprising the administration of an effective amount of arginine aspartate is disclosed.

3 Claims, No Drawings

METHOD FOR TREATING MEMORY DISTURBANCES USING ARGININE ASPARTATE

BACKGROUND OF THE INVENTION

Field of the Invention

This invention concerns a drug for treating memory disturbances, for example those caused by drugs such as benzodiazepines, for example diazepam, cholinolytics, for example scopolamine, or by electric shock treatments. The treatment is accomplished by repeated administration of arginine aspartate.

Arginine aspartate is a known product that was described in France in the special drug patents No. 1625 M and 106 CAM on Sept. 15, 1961 and Dec. 21, 1964, and in French Patent 2568124 of July 24, 1984. This product is the salt resulting from the reaction of equimolecular quantities of L-aspartic acid and L-arginine; the compound has the formula

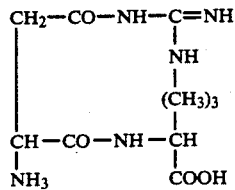

The physiological effects and a probable method of action of this product were described in these documents, which make therapeutic use of it in
- hyperammonemic conditions,
- mental and physical asthenia,
- and certain retardations of growth.

It has now been found surprisingly that this aspartate, when it is used orally, can be useful in certain memory disturbances. Up to now, among all of the pharmacological actions of arginine aspartate that are presently known, or of any other salt of arginine, none could suggest such a possibility. Furthermore, no bibliographic search made on the various salts of arginine or of aspartic acid suggests such possible activity.

Benzodiazepines and scopolamine are very widely used drugs, but they frequently involve a loss of memory: GOODMAN and GILMAN, The pharmacological basis of therapeutics, 7th Edition, pages 341-342, 133.

Electroshocks are therapy that is very useful in the treatment of patients afflicted with serious psychosis and major personality disturbances. Nevertheless, electroshock therapy has major secondary effects, memory disturbances, although the methods of application currently used have somewhat less severe side effects. For a review of electroshock therapy, refer to the article by SELVIN-B-L, Electroconvulsive therapy, 1987, Anesthesiology, 1987, 67, 367-385.

It has now been shown that arginine aspartate used orally greatly reduces the loss of memory in various models of amnesia induced in the mouse or the rat.

TOXICOLOGICAL RESULTS

Oral administration of various single doses of arginine aspartate to Sprague Dawley rats or to Swiss mice has shown that the 50% lethal doses (LD50) are above 20 g/kg of body weight in either of the two species.

Intraperitoneally, the LD50's in the rat and the mouse, respectively, are:

| SPECIES | LD50 (g/kg) | 95% confidence limits |
|---|---|---|
| Mouse | 9.7 | (9.4–9.9) |
| Rat | 8.50 | (8.1–8.8) |

The subacute toxicity study was carried out orally in the rat at daily doses of 1, 2, 5, and 5 g/kg for 4 weeks. No disturbance of the biochemical or hematological balances was observed. The anatomopathological study of the principal organs showed no lesions of toxic origin.

The chronic toxicity study was carried out in the beagle dog with oral administration at daily doses of 1, 5, and 10 g/kg for 6 months. Arginine aspartate administered at the dose of 10 g/kg caused the death of 2 animals in several weeks. This dose was reduced to 7.5 g/kg/day. After this modification, one death was still recorded. At the 2 strong doses, a clear increase of the frequency of diarrhea and the presence of considerable salivation were observed. No biological disturbance and no anatomopathological lesion were recorded, but a slight tendency toward hyperglycemia was found at the strong doses. A reversibility test showed that the clinical and biological symptomatologies disappeared starting with the discontinuation of the treatment, and that no sign of delayed toxicity occurred. Over a period of 6 months the limit of harmlessness in the beagle dog is between 1 and 5 g/kg/day.

PHARMACOLOGICAL RESULTS

In amnesia induced by scopolamine in the mouse according to the passive avoidance test described by GLICK-S-D, ZIMMERBERG-B, Behavorial Biology 1972, 7, 245-25, arginine aspartate administered orally at a dose of 2048 mg/kg after 7 administrations significantly antagonizes the amnesia induced by scopolamine. Piracetam shows comparable activity.

The passive avoidance test is carried out in an apparatus with two compartments, one light and one dark. An animal is placed in the light chamber. When the animal passes into the dark chamber a 0.3 mA electric shock is administered to it until it returns to the light chamber; this is the learning phase A. 24 hours later, the animal is again placed in the light chamber and the delay before passing into the dark chamber is measured; this is the test phase E. An increase of this time of delay reflects the animal's memory of the electric shock received the previous day. Administration of scopolamine 30 minutes before the test phase E reduces this remembrance.

The passive avoidance test accordingly has two phases; a learning phase A in which the leaving time is measured, and a test phase E in which the leaving time is again measured. The learning phase A is carried out on Day 4, after intraperitoneal administration of the amnestic agent (scopolamine 1 mg/kg 30 minutes before the learning phase A). The test phase E is carried out on Day 5. We indicate in the table below the results obtained with arginine aspartate orally in one dose of 2048 mg/kg or chronically at an oral dose of 2048 mg/kg, 7 administrations, 2 administrations/day, and for piracetam administered in one dose of 2048 mg/kg orally.

All of the experiments were carried out blind with 20 animals per lot.

| Arginine aspartate, orally | | | | Scopolamine, ip | Time of delay before leaving, seconds | Student test |
|---|---|---|---|---|---|---|
| D1 | D2 | D3 | D4 | A D4 | E D5 | |
| 0 | | | | 0 | 175.9 ± 3.9 | |
| 0 | | | | 1 | 123.7 ± 11.1 | 4.543* |
| 0 | | | | 2048  1 | 119.0 ± 14.7 | 0.264** |
| 2048 | | | | 2048  1 | 162.9 ± 6.9 | 3.091** |
| Piracetam 0 | | | | 2048  1 | 171.5 ± 4.2 | 4.139** |

*Compared with the controls without scopolamine
**Compared with the controls with scopolamine In amnesia induced by diazepam, we show in the table below the results obtained with arginine aspartate administered in one dose of 2048 mg/kg orally, and with piracetam administered in one dose of 2048 mg/kg orally, using the same passive avoidance test as above.

All of the experiments were carried out blind with 20 animals per lot.

| Arginine aspartate, orally | Diazepam, ip | Time of delay before leaving, seconds | Student test |
|---|---|---|---|
| D1 | A D1 | E D2 | |
| 0 | 0 | 175.3 ± 3.3 | |
| 0 | 1 | 116.0 ± 15.2 | 3.923* |
| 2048 | 1 | 157.1 ± 12.6 | 2.135** |
| Piracetam 2048 | 1 | 173.1 ± 3.9 | 3.738** |

In amnesia induced by electroshock, the activity of arginine aspartate was determined in the rat using the same passive avoidance test.

We show in the table below the results obtained with arginine aspartate administered chronically at a dose of 500 mg/kg orally, 7 administrations, 1 administration/day.

| Arginine aspartate, orally | | | | | | Electroshock | Time of delay before leaving, seconds | Fisher test |
|---|---|---|---|---|---|---|---|---|
| D1 | D2 | D3 | D4 | D5 | D6 | A D7 | E D8 | |
| 0 | | | | | | yes | 34 | |
| 500 | | | | | | yes | 104 | 3.69 |

It can be concluded from these three pharmacological tests that repeated administration of arginine aspartate clearly prevents the memory disturbances caused by the administration of treatments considered to be amnestic.

This pharmacological activity of arginine aspartate on a specific function of the central nervous system is surprising, considering the knowledge acquired up to now of the properties of this substance, specifically the stimulation of protein anabolism explaining its antiasthenic action.

We claim:

1. A method for treating a patient suffering from memory disturbances that comprises administering an effective amount of arginine aspartate to a patient whose memory disturbance has been caused by the administration of benzodiazepines, cholinolytics or electroshock.

2. The method of claim 1 wherein the total dose of arginine aspartate is between 100 and 1000 mg/kg/day.

3. The method of claim 2 wherein the dose of arginine aspartate is administered in the form of one or more dosage units.

* * * * *